United States Patent [19]

Watanabe et al.

[11] Patent Number: 5,171,919
[45] Date of Patent: Dec. 15, 1992

[54] PROCESS FOR PRODUCING PROPYLENE BASED OLIGOMERS

[75] Inventors: Masami Watanabe; Nobuhide Ishihara, both of Sodegaura, Japan

[73] Assignee: Idemitsu Kosan Co., Ltd., Tokyo, Japan

[21] Appl. No.: 777,788

[22] Filed: Oct. 17, 1991

[30] Foreign Application Priority Data

Oct. 17, 1990 [JP] Japan .................................. 2-278408

[51] Int. Cl.$^5$ ........................... C07C 2/26; C07C 2/32
[52] U.S. Cl. ................................. 585/523; 585/512; 585/513
[58] Field of Search .............. 585/510, 511, 512, 513, 585/523

[56] References Cited

U.S. PATENT DOCUMENTS

| | | | |
|---|---|---|---|
| 4,658,078 | 4/1987 | Slaugh et al. | 585/512 |
| 4,665,262 | 5/1987 | Graves | 585/524 |
| 4,704,491 | 11/1987 | Tsutsui et al. | 585/512 |
| 4,814,540 | 3/1989 | Watanabe et al. | 585/523 |
| 5,030,790 | 7/1991 | Sergienko et al. | 585/513 |
| 5,043,515 | 8/1991 | Slaugh et al. | 585/512 |

*Primary Examiner*—Anthony McFarlane
*Attorney, Agent, or Firm*—Oblon, Spivak, McClelland, Maier & Neustadt

[57] ABSTRACT

A process for producing a propylene based oligomer which comprises polymerizing propylene alone or propylene and an olefin other than propylene in the presence of a catalyst comprising:

(A) a transition metal compound represented by the general formula (I):

$$(R_5C_5)_m MX_{4-m} \qquad (I)$$

wherein $R_5C_5$ may be the same as or different from each other and is a hydrocarbon group-substituted cyclopentadienyl group; M is a zirconium atom or hafnium atom; X may be the same as or different from each other and is a hydrogen atom, halogen atom or hydrocarbon group; m is an integer of from 1 to 4; and (B) a compound capable of forming an ionic complex when reacted with a transition metal compound, is disclosed.

According to the present invention, a propylene oligomer can be produced without using a promoter such as aluminoxane or with use of a small amount of an organoaluminum compound. Therefore, according to the present invention, such propylene based oligomers can be produced at reduced cost with use of the process comprising a simplified deashing step.

4 Claims, No Drawings

PROCESS FOR PRODUCING PROPYLENE BASED OLIGOMERS

BACKGROUND OF THE INVENTION

1. Field of the Invention

The present invention relates to a process for producing a propylene oligomer or an oligomer of propylene and an olefin or more than two olefins other than propylene, which can be effectively used as starting materials for chemical synthesis, starting materials for polymers, lubricating oil substrates, cosmetics and the like.

2. Related Art

Propylene oligomers and oligomers of propylene and an olefin or more than two olefins other than propylene have been used as starting materials for chemical synthesis, starting materials for polymers, lubricating oil substrates, cosmetics and the like.

As a process for producing the above propylene based oligomers, there have been heretofore known a process which comprises reacting propylene alone or propylene and the other olefin, using a catalyst composed of an alkyl-substituted cyclopentadienyl compound containing zirconium and/or hafnium; and aluminoxane (Japanese Patent Appln. Laid-Open Gazette No. Hei 1-207248; U.S. Pat. No. 4,814,540).

However, in the above-mentioned process, after polymerization, deashing treatment for the resultant product should be sufficiently conducted since the aluminoxane as promotor should be used in a large amount as compared with the amount of the transition metal compound as main catalyst component to provide sufficient activity and a large amount of the aluminum compound is used. Since the aluminoxane is expensive, the amount thereof used should be drastically reduced. It is desirable not to use the aluminoxane.

SUMMARY OF THE INVENTION

In view of the above-mentioned situations, the present invention has its object to provide a process capable of producing a propylene based oligomer without using a promotor such as aluminoxane or with use of a small amount of an organoaluminum compound. Such process makes it possible to simplify the deashing step, resulting in simplification of the whole process, and thus provides cost reduction.

To achieve the above object, there is provided a process for producing a propylene based oligomer which comprises polymerizing propylene alone or propylene and an olefin or more than two olefins other than propylene in the presence of a catalyst comprising:

(A) a transition metal compound represented by the general formula (I):

$$(R_5C_5)_mMX_{4-m} \quad (I)$$

wherein $R_5C_5$ may be the same as or different from each other and is a hydrocarbon group-substituted cyclopentadienyl group; M is a zirconium atom or hafnium atom; X may be the same as or different from each other and is a hydrogen atom, halogen atom or hydrocarbon group; m is an integer of from 1 to 4; and (B) a compound capable of forming an ionic complex when reacted with a transition metal compound; and optionally, (C) an organoaluminum compound.

According to the present invention, a propylene oligomer having a polymerization degree of 2 to 20, preferably 2 to 15 and containing a terminal vinyl group, or an oligomer of propylene and an olefin other than propylene, can be mainly produced with high efficiency and high selectivity, without using a promotor such as aluminoxane or with use of a small amount of an organoaluminum compound. Therefore, according to the present invention, such propylene based oligomers can be produced at reduced cost with use of the process comprising a simplified deashing step.

The other objects and advantages of the present invention will be apparent from the following description.

DESCRIPTION OF THE PREFERRED EMBODIMENTS

The present invention will be described in more detail below.

In Compound (A) used in the present invention, the hydrocarbon groups as represented by R or X in the above Formula (I) are not particularly limited, but include a $C_{1-20}$ alkyl group, aryl group and arylalkyl group. The $C_{1-20}$ alkyl groups include, for example, a methyl group, ethyl group, propyl group, isopropyle group, butyl group, isobutyl group, t-butyl group, amyl group, hexyl group, heptyl group, octyl group, nonyl group, capryl group, undecyl group, lauryl group, tridecyl group, myristyl group, pentadecyl group, cetyl group, heptadecyl group, stearyl group, nanodecyl group, eicosyl group and the like. Further, the $C_{1-20}$ aryl group or arylalkyl group include, for example, a phenyl group, benzyl group and phenethyl group. Examples of $C_{1-20}$ alkylaryl groups are p-tryl group and p-n-butylphenyl group. Further, m is preferably 1 or 2, more preferably 2.

More specifically, suitable examples of Compound (I) include $[(CH_3)_5C_5]_2Hf(CH_2Ph)_2$; $[(CH_3)_5C_5]_2Zr(CH_2Ph)_2$; $[(CH_3)_5C_5]_2HfPh_3$; $[(CH_3)_5C_5]_2ZrPh_3$; $[(CH_3)_5C_5]_2Hf(C_6H_4\text{-p-}CH_3)_2$; $[(CH_3)_5C_5]_2Zr(C_6H_4\text{-p-}CH_3)_2$; $[(CH_3)_5C_5]_2Hf(CH_3)_2$; $[(CH_3)_5C_5]_2Zr(CH_3)_2$; $[(C_2H_5)_5C_5]_2Hf(CH_3)_2$; $[(C_2H_5)_5C_5]_2Zr(CH_3)_2$; $[(n\text{-}C_3H_7)_5C_5]_2Hf(CH_3)_2$; $[(n\text{-}C_3H_7)_5C_5]_2Zr(CH_3)_2$; $[(CH_3)_5C_5]_2HfH(CH_3)$; $[(CH_3)_5C_5]_2ZrH(CH_3)$; $[(C_2H_5)_5C_5]_2HfH(CH_3)$; $[(C_2H_5)_5C_5]_2ZrH(CH_3)$; $[(C_3H_7)_5C_5]_2HfH(CH_3)$; $[(C_3H_7)_5C_5]_2ZrH(CH_3)$; $[(CH_3)_5C_5]_2Hf(H)_2$; $[(CH_3)_5C_5]_2Zr(H)_2$; $[(C_2H_5)(CH_3)_4C_5]_2Hf(CH_3)_2$; $[(C_2H_5)(CH_3)_4C_5]_2Zr(CH_3)_2$; $[(n\text{-}C_3H_7)(CH_3)_4C_5]_2Hf(CH_3)_2$; $[(n\text{-}C_3H_7)(CH_3)_4C_5]_2Zr(CH_3)_2$; $[(n\text{-}C_4H_9)(CH_3)_4C_5]_2Hf(CH_3)_2$; $[(n\text{-}C_4H_9)(CH_3)_4C_5]_2Zr(CH_3)_2$; $[(CH_3)_5C_5]_2HfCl_2$; $[(CH_3)_5C_5]_2ZrCl_2$; $[(CH_3)_5C_5]_2HfH(Cl)$; and $[(CH_3)_5C_5]_2ZrH(Cl)$. Of these compounds, more suitable compounds are pentaalkylcyclopentadienyl compounds such as $[(CH_3)_5C_5]_2Hf(CH_2Ph)_2$; $[(CH_3)_5C_5]_2Zr(CH_2Ph)_2$; $[(CH_3)_5C_5]_2Hf(CH_3)_2$; $[(CH_3)_5C_5]_2Zr(CH_3)_2$; $[(CH_3)_5C_5]_2HfH(CH_3)$; $[(CH_3)_5C_5]_2ZrH(CH_3)$; $[(CH_3)_5C_5]_2Hf(H)_2$; $[(CH_3)_5C_5]_2Zr(H)_2$; $[(C_2H_5)(CH_3)_4C_5]_2Hf(CH_3)_2$; $[(C_2H_5)(CH_3)_4C_5]_2Zr(CH_3)_2$; $[(n\text{-}C_3H_7)(CH_3)_4C_5]_2Hf(CH_3)_2$; $[(n\text{-}C_3H_7)(CH_3)_4C_5]_2Zr(CH_3)_2$; $[(n\text{-}C_4H_9)(CH_3)_4C_5]_2Hf(CH_3)_2$; and $[(n\text{-}C_4H_9)(CH_3)_4C_5]_2Zr(CH_3)_2$ with the hafnium compounds being particularly preferred.

In addition, Compounds (I) can be used alone or in combination.

Compounds (B) as used in the present invention may not be specifically limited and may be any compounds capable of forming an ionic complex when reacted with a transition metal compound, for example, a compound composed of a cation and an anion wherein a plural of groups are connected to an element, particularly a coordination complex compound. Suitable Compounds (B) may be represented by the following formula (II), (III) or (IV):

$$([L^1-H]^{g+})_h([M^2X^1X^2 \ldots X^n]^{(n-m)-}); \quad (II)$$

$$([L^2]^{g+})_h([M^3X^1X^2 \ldots X^n]^{(n-m)-}); \quad (III)$$

$$([L^1-Z]^{g+})_h([M^2X^1X^2 \ldots X^n]^{(n-m)-}); \quad (IV)$$

wherein $L^2$ is $M^4$, $R^2R^3M^5$ or $R^4{}_3C$.

In Formula (II), (III) or (IV), $L^1$ is a Lewis base; Z is a hydrocarbon group such as an alkyl group, aryl group, arylalkyl group or alkylaryl group; $M^2$ and $M^3$ are independently elements selected from the groups of VB, VIB, VIIB, VIII, IB, IIB, IIIA, IVA and VA of the Periodic Table; $M^4$ is a transition metal, preferably a metal selected from the groups of IB, IIB and VIII of the Periodic Table; $M^5$ is a metal selected from the VIII group of the Periodic Table; $X^1$ to $X^n$ are independently a hydrogen atom, dialkylamino group, alkoxy group, aryl group, substituted aryl group, aryloxy group, alkyl group, substituted alkyl group, organometalloid group or halogen atom; $R^2$ and $R^3$ are independently cyclopentadienyl group, substituted cyclopentadienyl group, indenyl group or fluorenyl group; $R^4$ is an alkyl group, substituted alkyl group, aryl group, substituted aryl group, arylalkyl group, substituted arylalkyl group, alkylaryl group or substituted alkylaryl group; $R_4$ may be the same as or different from each other; m is a valency of $M^2$ and $M^3$ and is an integer of 1 to 7; n is an integer of 2 to 8; g is an ion value number of $L^1$-H and $L^2$, and is an integer of 1 to 7; and h is an integer of at least 1; and i is specified by the formula: $i = h \cdot g/(n-m)$.

Examples of the above Lewis bases are ethers such as dimethyl ether, diethyl ether, tetrahydrofuran; thioethers such as tetrahydrothiophene; esters such as ethylbenzoate; nitrils such as acetonitrile and benzonitrile; amines such as dimethylaniline, pyridine, 2-cyanopyridine, 3-cyanopyridine, 4-cyanopyridine, triethylamine, 2,2-bipyridine and phenanthroline; and phosphines such as triethylphosphine and triphenylphosphine.

Examples of Z are a methyl group, ethyl group, benzyl group and trityl group. Examples of $M^2$ and $M^3$ are, for example, B, Al, Si, P, As and Sb. Examples of $M^4$ are Af and Cu. Examples of $M^5$ are Fe, Co and Ni. Examples of $X^1$ to $X^n$ include dialkylamino groups such as a dimethylamino group and diethylamino group; alkoxy groups such as a methoxy group, ethoxy group and n-butoxy group; ary groups or substituted aryl groups such as those having 6 to 20 carbon atoms such as a phenyl group, 4-tryl group, 3,5-xylyl group, benzyl group, pentafluorophenyl group, 3,5-di(trifluoromethyl)phenyl group and 4-ter-butylphenyl group; aryloxy groups such as a phenoxy group, 2,6-dimethylphenoxy group and naphthyloxy group; alkyl groups such as those having 1 to 20 carbon atoms such as a methyl group, ethyl group, n-propyl group, iso-propyl group, n-butyl group, n-octyl group and 2-ethylhexyl group; organometalloid groups such as a pentamethylantimony group; trimethylsilyl group and trimethylstannyl group; and halogens such as F, Cl, Br and I. Examples of substituted cyclopentadienyl groups represented by $R^2$ and $R^3$ include a methylcyclopentadienyl group, butylcyclopentadienyl group, pentamethylcyclopentadienyl group, trifluoromethyltetramethylcyclopentadienyl group, nitrocyclopentadienyl group, ethoxycarbonylcyclopentadienyl group and cyanocyclopentadienyl group. Examples of $R^4$ are a methyl group, ethyl group, phenyl group, p-tryl group, p-methoxyphenyl group and p-dimethylaminophenyl group.

Of those compounds represented by Formula (II), (III) or (IV), the following compounds can be particularly used as preferred ones.

Compounds Represented by Formula (II)

Tetrakisphenylboric acid trimethylammonium, tetrakisphenylboric acid triethylammonium, tetrakisphenylboric acid tri(n-butyl)ammonium, tetrakis(pentafluorophenyl)boric acid dimethyl anilinium, tetrakis(pentafluorophenyl)boric acid triethylammonium, tetrakis(pentafluorophenyl)boric acid tri(n-butyl)ammonium, and hexafluoroarsenic acid triethylammonium.

Compounds Represented by Formula (III)

Tetrakisphenylboric acid ferrocenium, tetrakisphenylboric acid trityl, tetrakis(pentafluorophenyl)boric acid ferrocenium, tetrakis(pentafluorophenyl)boric acid methylferrocenium, tetrakis(pentafluorophenyl)boric acid decamethylferrocenium, silver tetrakis(pentafluorophenyl) borate, tetrakis(pentafluorophenyl)boric acid trityl, hexafluoroarsenical silver, hexafluorosilver antimonate, and tetrakisfluorosilver borate.

Compounds Represented by Formula (IV)

Tetrakis(pentafluorophenyl)boric acid(N-benzyl-2-cyanopyridinium); tetrakis(pentafluorophenyl)boric acid(N-benzyl-3-cyanopyridinium); tetrakis(pentafluorophenyl)boric acid(N-benzyl-4-cyanopyridinium); tetrakis(pentafluorophenyl)boric acid(N-methyl-2-cyanopyridinium); tetrakis(pentafluorophenyl)boric acid(N-methyl-3-cyanopyridinium); tetrakis(pentafluorophenyl)boric acid(N-methyl-4-cyanopyridinium); tetrakis(pentafluorophenyl)boric acid trimethylanilinium; tetrakis(pentafluorophenyl)boric acid trimethyl(m-trifluoromethylphenyl)ammonium; and tetrakis(pentafluorophenyl)boric acid benzylpyridinium.

The organoalkylaluminum compounds, Component (C) are not particularly limited, but include, for example, those compounds represented by the following Formula (V):

$$AlR^5{}_3 \quad (V)$$

wherein $R^5$ is a hydrogen atom, a halogen atom or an alkyl group having 1 to 8 carbon atoms.

Examples of the organoaluminum compounds are triisobutylaluminum, hydrogenated diisobutylaluminum, trimethylaluminum, triethylaluminum and diethylaluminum chloride.

In addition to the above compounds, aluminoxanes such as methylaluminoxane and ethylaluminoxane can be used as Component (C).

The catalysts as used in the present invention comprises the above Components (A) and (B), and optionally, Component (C).

In this case, the use conditions are not limited; however it is preferable to adjust a use ratio of Component (A) to Component (B) to 1:0.1 to 1:100, more preferably 1:0.5 to 1:10, most preferably 1:0.8 to 1:5. It is possible that Components (A) and (B) are preliminarily reacted and the reaction product is separated, washed and used for polymerization. It is also possible that Components (A) and (B) themselves are directly used for the polymerization.

In addition, Component (C) is used in an amount to provide a Component (C) to Component (A) molar ratio of from 1 to 1000, preferably from 10 to 700, more preferably 20 to 500.

In this case, the use of Component (C) is not particularly limited. For example, a reaction product of Components (A) and (B), and Component (C) can be added to the polymerization system; a recation product of Components (A) and (C), and Component (B) can be added; and Components (A), (B) and (C) can be simultaneously or separately added.

In the present invention, propylene alone or propylene and an olefin other than propylene are polymerized in the presence of the above-mentioned catalyst.

The other olefins than propylene are not particularly limited, but usually include alpha-olefins having 2 to 16 carbon atoms, preferably 2 to 8 carbon atoms. Alpha-olefins having a terminal vinyl group can be preferably used.

The alpha-olefins which can be preferably used, include for example, ethylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1,4-pentadiene, 1,5-heptadiene, 1,7-octadiene, 1,9-decadiene, 4methyl-1-pentene, neohexene, vinylcyclohexene, 4-vinylcyclohexence and the like.

Of these, particularly preferred are ethylene, 1-butene, 1-pentene, 1-hexene, 1-heptene and 1-octene.

The above olefins other than propylene may be used alone or in combination.

The ratio of propylene and an olefin other than propylene used is not limited, but it is possible to adjust the component ratio of the resultant propylene based oligomer by appropriately selecting the ratio of propylene to the other olefins. To increase selectivity of a compound containing a terminal vinyl group, it is desirable to increase a ratio of propylene to the other olefins.

In addition, propylene and the olefins other than propylene can be separately supplied to the reaction system, or can be preliminarily blended and supplied.

In the oligomerization reaction of propylene alone or propylene and the other olefins, the reaction temperature is not particularly limited, but usually ranges from 0° to 100° C., preferably from 20° to 80° C. The reaction pressure may be appropriately selected. The oligomerization reaction can be carried out at, for example, as low as 10 Kg/cm²G or low or at normal pressure if desired.

The reaction temperature will be further described. If the reaction temperature is low, the resultant products tend to have high degree of polymerization. On the contrary, if the reaction temperature is high, products having a low degree of polymerization, such as a dimer and trimer can be obtained. Thus, the reaction temperature can be determined depending upon a desired product. However, if the temperature is outside the range of 0° to 100° C., there is a possibility that the catalyst activity may be lowered.

In the low polymerization reaction of propylene alone or the low polymerization reaction of propylene and the other olefins, a solvent can be used.

The solvents include, for example, aromatic hydrocarbons such as benzene, toluene, xylene, ethylbenzene, cumene, mesitylene, naphthalene, tetralin, butylbenzene, p-cymene, cyclohexylbenzene, diethylbenzene, pentylbenzene, dispentylbenzene, dodecylbenzene and biphenyl; aliphatic hydrocarbons such as 2-methylbutane, hexane, 2-methylpentane, 2,2-dimethylbutane, 2,3-dimethylbutane, heptane, octane, 2,2,3-trimethylpentane, isooctane, nonane, 2,2,5-trimethylhexane, decane and dodecane; alicyclic hydrocarbons such as cyclopentane, methylcyclopentane, cyclohexane, methylcyclohexane, ethylcyclohexane and decalin; petroleum ether, petroleum benzine, petroleum naphtha, ligroin, industrial gasoline, kerosene; and solvents having a polar group such as chlorobenzene, phenyl methyl ether, dimethylaniline and phenyl methyl thioether.

The polymerization method can be selected from any methods such as solution polymerization, bulk polymerization and vapor polymerization, but the solution polymerization is preferred in view of catalyst activities.

According to the process for production of propylene based oligomers of the present invention, a mixture of the compounds having a terminal vinyl group, represented by the following general formula:

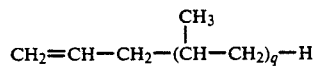

(wherein q is a real number of from 1 to 20, preferably from 1 to 15.) can be mainly produced at high selectivity under simple and mild conditions.

According to the inventors' further investigation, it was found that in the low polymerization of propylene alone or propylene and the other olifins, the presence of hydrogen improves polymerization activities, and also improves olefin conversion rate without lowering selectivity of olefins since no hydrogenation of olefins takes place.

In other words, propylene based oligomers can be produced with high selectivity by polymerizing propylene alone or propylene and the other olefin in the presence of a catalyst comprising the above-mentioned hydrocarbon group-substituted cyclopentadienyl compound containing zirconium or hafnium, and the above-mentioned compound capable of forming an ionic complex with a metal; and hydrogen.

The hydrogen which can be used in the present invention includes, for example, one obtained from modification of aqueous gas, gasification of petroleums, complete gassification of coal, modification of natural gas and so on.

The amount of hydrogen used is not limited, but may usually be in the range of 1 to 100 mol %, preferably from 5 to 20 mol % based on propylene as starting material.

The kind and the component ratio of the propylene based oligomers obtained according to the process of the present invention, may be adjusted depending upon the kind of olefins other than propylene, ratio of the olefin to propylene used, the reaction conditions and the like.

EXAMPLES AND COMPARATIVE EXAMPLES

The present invention will be described in more detail with reference to the following Examples and Comparative Examples which are not intended to limit the scope of the invention.

EXAMPLE 1

To an autoclave with an inner volume of 1 liter, were charged 400 ml of toluene; $3 \times 10^{-3}$ mol (2 mol/l-toluene solution) of triisobutylaluminum (TIBA) as Component (C); $1 \times 10^{-5}$ mol (0.1 mol/l-toluene solution) of bis(pentamethylcyclopentadienyl)hafnium demethyl as transition metal component (Component (A)); and $1 \times 10^{-5}$ mol (0.05 mol/l-toluene solution) of tetra(pentafluorophenyl)boric acid triethylanmonium as coordination complex compound (Component (B)) in this order under argon stream. Then, the obtained mixture was heated to 55° C.

After 1 Kg/cm² of hydrogen was introduced, the reaction was carried out at 55° C. for 4 hours while propylene was continuously introduced to keep propylene pressure at 9 Kg/cm²G.

After completion of the reaction, the reaction product was deashed with 150 ml of 3N·HCl and the toluene phase was removed. The obtained solution was analyzed using gas chromatography, infra red absorption spectrum and proton nuclear magnetic resonance spectrum.

As a result, it was found that the obtained oligomer had a molar ratio of a terminal vinyl group to a terminal vinylidene group of 98:2, and contained as main component the following products.

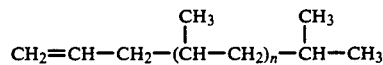

wherein n is an integer of 0 or more.

Further, the total yield was 330 g. As a result of further analysis, the obtained product had 108 g of dimer, 96 g of trimer and 81 g of tetramer.

Further, as a result of detailed analysis on the dimer, it was found that the dimer contained 99% of 4-methyl-1-pentene and 1% of 2-methyl-1-pentene.

The results were as shown in Table 1.

EXAMPLE 2 TO 13

The same procedures of Example 1 were repeated except that the experiment conditions were changed as indicated in Table 1.

The results are as shown in Table 1.

TABLE 1

| Example No. | Catalyst Component (a) (mmol) | Catalyst Component (b) (mmol) | Catalyst Component (c) (mmol) | H₂ Partial Pressure (Kg/cm²) | Propylene Pressure *7 (g/cm²G) |
|---|---|---|---|---|---|
| Example 1 | [(CH₃)₅C₅]₂Hf(CH₃)₂ 0.01 | [Et₃NH][B(C₆F₅)₄] 0.01 | TIBA *4 3 | 1 | 9 |
| Example 2 | [(CH₃)₅C₅]₂Zr(CH₃)₂ 0.01 | [Et₃NH][B(C₆F₅)₄] 0.01 | TIBA 3 | 1 | 9 |
| Example 3 | [(CH₃)₅C₅]₂Hf(CH₂Ph)₂ 0.01 | [Et₃NH][B(C₆F₅)₄] 0.01 | TIBA 3 | 1 | 9 |
| Example 4 | [(CH₃)₅C₅]₂Zr(CH₂Ph)₂ 0.01 | [Et₃NH][B(C₆F₅)₄] 0.01 | TIBA 3 | 1 | 9 |
| Example 5 | [n-Bu(CH₃)₄C₅]₂Hf(CH₃)₂ 0.01 | [Et₃NH][B(C₆F₅)₄] 0.01 | TIBA 3 | 1 | 9 |
| Example 6 | [n-Bu(CH₃)₄C₅]₂Zr(CH₃)₂ 0.01 | [Et₃NH][B(C₆F₅)₄] 0.01 | TIBA 3 | 1 | 9 |
| Example 7 | [(CH₃)₅C₅]₂Hf(CH₃)₂ 0.01 | [Fc][B(C₆F₅)₄] *5 0.01 | TIBA 3 | 1 | 9 |
| Example 8 | [(CH₃)₅C₅]₂Hf(CH₃)₂ 0.01 | [Et₃NH][B(C₆F₅)₄] 0.01 | TEA *6 3 | 1 | 9 |
| Example 9 | [(CH₃)₅C₅]₂Hf(CH₃)₂ 0.01 | [Et₃NH][B(C₆F₅)₄] 0.01 | TIBA 3 | 1 | 9 |
| Example 10 | [(CH₃)₅C₅]₂Hf(CH₃)₂ 0.01 | [Et₃NH][B(C₆F₅)₄] 0.01 | TIBA 3 | 1 | 9 |
| Example 11 | [(CH₃)₅C₅]₂Hf(CH₃)₂ 0.10 | [Et₃NH][B(C₆F₅)₄] 0.10 | — | — | 9 |
| Example 12 | [(CH₃)₅C₅]₂Hf(CH₃)₂ 0.01 | [Et₃NH][B(C₆F₅)₄] 0.01 | TIBA 3 | — | 9 |
| Example 13 | [(CH₃)₅C₅]₂Hf(CH₃)₂ 0.10 | [Et₃NH][B(C₆F₅)₄] 0.10 | — | 1 | 9 |

| Example No. | Temp. (°C.) | Time (hr) | Total Yield (g) | Dimer (g) | Trimer (g) | Selectivity (%) (*1/*2) | Selectivity (%) *3 (4MP1) |
|---|---|---|---|---|---|---|---|
| Example 1 | 55 | 4 | 300 | 108 | 96 | 98/2 | 99 |
| Example 2 | 55 | 4 | 250 | 40 | 60 | 92/8 | 98 |
| Example 3 | 55 | 4 | 320 | 115 | 100 | 98/2 | 99 |
| Example 4 | 55 | 4 | 280 | 45 | 62 | 92/8 | 98 |
| Example 5 | 55 | 4 | 280 | 112 | 67 | 98/2 | 99 |
| Example 6 | 55 | 4 | 240 | 50 | 59 | 92/8 | 98 |
| Example 7 | 55 | 4 | 320 | 110 | 101 | 98/2 | 99 |
| Example 8 | 55 | 4 | 240 | 81 | 64 | 98/2 | 99 |
| Example 9 | 80 | 4 | 80 | 61 | 12 | 92/8 | 95 |
| Example 10 | 30 | 4 | 340 | 66 | 71 | 98/2 | 99 |
| Example 11 | 55 | 4 | 31 | 16 | 10 | 98/2 | 100 |
| Example 12 | 55 | 4 | 35 | 14 | 10 | 98/2 | 100 |

TABLE 1-continued

| | | | | | | | |
|---|---|---|---|---|---|---|---|
| Example 13 | 55 | 4 | 75 | 32 | 24 | 98/2 | 99 |

*1: Propylene origomer having a terminal vinyl group
*2: Propylene origomer having a terminal vinylidene group
*3: 4-methyl-penten
*4: Triisobutylaluminum
*5: Ferrocenium cation
*6: Triethylaluminum
*7: Total Pressure

EXAMPLE 14

To an autoclave with an inner volume of 1 liter, were charged 400 ml of toluene; $3 \times 10^{-3}$ mol (2 mol/1-toluene solution) of triisobutylaluminum (TIBA) as Component (C); $1 \times 10^{-5}$ mol (0.1 mol/1-toluene solution) of bis(petamethylcyclopentadienyl)hafnium demethyl as transition metal component (Component (A)); and $1 \times 10^{-5}$ mol (0.05 mol/1-toluene solution) of tetra(pentafluorophenyl)boric acid triethylanmonium as coordination complex compound (Component (B)) in this order under argon stream. Then, the obtained mixture was heated to 55° C.

Then, 1 Kg/cm² of hydrogen and 20 g of 1-butene were introduced to the reaction system in this order. Thereafter propylene was introduced to keep propylene pressure at 2 Kg/cm²G, and the reaction was carried out at 55° C. for 4 hours.

After completion of the reaction, the reaction product was deashed with 150 ml of 3N·HCl and the toluene phase was removed. The obtained solution was analyzed using gas chromatography, infra red absorption spectrum and proton nuclear magnetic resonance spectrum.

As a result, it was found that the total yield was 24.5 g.

The results were as shown in Table 2.

EXAMPLES 15 TO 18

The same procedures of Example 14 were repeated except that the experiment conditions were changed as indicated in Table 2.

TABLE 2

| Example No. | Catalyst Component (a) (mmol) | Catalyst Component (b) (mmol) | Catalyst Component (c) (mmol) | $H_2$ Partial Pressure (Kg/cm²) | Propylene Partial Pressure (Kg/cm²G) |
|---|---|---|---|---|---|
| Example 14 | $[(CH_3)_5C_5]_2Hf(CH_3)_2$ 0.01 | $[Et_3NH][B(C_6F_5)_4]$ 0.01 | TIBA 3 | 1 | 2 |
| Example 15 | $[(CH_3)_5C_5]_2Hf(CH_3)_2$ 0.01 | $[Et_3NH][B(C_6F_5)_4]$ 0.01 | TIBA 3 | 1 | 5 |
| Example 16 | $[(CH_3)_5C_5]_2Hf(CH_3)_2$ 0.01 | $[Et_3NH][B(C_6F_5)_4]$ 0.01 | TIBA 3 | 1 | 5 |
| Example 17 | $[(CH_3)_5C_5]_2Hf(CH_3)_2$ 0.01 | $[Et_3NH][B(C_6F_5)_4]$ 0.01 | TIBA 3 | 1 | 5 |
| Example 18 | $[(CH_3)_5C_5]_2Zr(CH_3)_2$ 0.01 | $[Et_3NH][B(C_6F_5)_4]$ 0.01 | TIBA 3 | 1 | 5 |

| Example No. | Kind of Comonomer (g) | Total Yield (g) | Propylen Dimer (g) | Selectivity (*1/*2) | Codime (g) | Selectivity (%) *3 (*3/*4) |
|---|---|---|---|---|---|---|
| Example 14 | 1-ブテン 20 | 24.5 | 9.6 | 86/14 | 6.4 *5 | 79/21 |
| Example 15 | 1-ブテン 40 | 55.9 | 15 | 90/10 | 8.3 *5 | 78/22 |
| Example 16 | 1-ヘキセン 40 | 39.0 | 14.5 | 84/16 | 6.5 *6 | 80/20 |
| Example 17 | 1-ヘプテン 40 | 34.2 | 13.9 | 85/15 | 7.0 *7 | 83/17 |
| Example 18 | 1-ブテン 40 | 54.8 | 7.0 | 80/20 | 3.1 *5 | 71/29 |

*1: 4-methyl-1-penten
*2: 2-methyl-1-penten
*3: Propylene origomer having a terminal vinyl group
*4: Propylene origomer having a terminal vinylidene group
*5: 4-methyl-1-hexene
*6: 4-methyl-1-heptone
*7: 4-methyl-1-octene

EXAMPLES 19 TO 22

The same procedures of Example 1 were repeated except that the experiment conditions were changed as indicated in Table 3.

The results are as shown in Table 3.

COMPARATIVE EXAMPLES 1 AND 2

The same procedures of Examples 21 or 22 were repeated except that methylaluminoxane was used instead of Component (b), or Component (c).

The results are as shown in Table 3.

TABLE 3

| Example No. | Catalyst Component (a) (mmol) | Catalyst Component (b) (mmol) | Catalyst Component (c) (mmol) |
|---|---|---|---|
| Example 19 | $[(CH_3)_5C_5]_2Hf(CH_3)_2$ 0.01 | $[PhNM_{e2}H][B(C_6F_5)_4]$ 0.01 | TIBA 3 |

TABLE 3-continued

| Example 20 | [(CH₃)₅C₅]₂Hf(CH₃)₂ 0.01 | [MeCN][B(C₆F₅)₄]  0.01 | TIBA 3 |

| Example 21 | [(CH₃)₅C₅]₂HfCl₂ 0.01 | [PhNM$_{e2}$H][B(C₆F₅)₄] 0.01 | TIBA 3 |
| Example 22 | [(CH₃)₅C₅]ZrCl₂ 0.01 | [PhNM$_{e2}$H][B(C₆H₅)₄] 0.01 | TIBA 3 |
| Comp. Ex. 1 | [(CH₃)₅C₅]₂HfCl₂ 0.01 | Methylaluminoxane 6 (per aluminum atom) | — |
| Comp. Ex. 2 | [(CH₃)₅C₅]₂ZgCl₂ 0.01 | Methylaluminoxane 6 (per aluminum atom) | — |

| Example No. | H₂ Partial Pressure (Kg/cm²) | Propylene Pressure *4 (Kg/cm²G) | Temp. (°C.) | Time (Hr) | Total Yield (g) | Dimer (g) | Trimer (g) | Selectivity (%) (*1/*2) | Selectivity (%) *3 (4MP1) |
|---|---|---|---|---|---|---|---|---|---|
| Example 19 | 1 | 9 | 55 | 4 | 360 | 84 | 82 | 98/2 | 99 |
| Example 20 | 1 | 9 | 55 | 4 | 240 | 60 | 54 | 98/2 | 99 |
| Example 21 | 1 | 9 | 55 | 4 | 260 | 78 | 74 | 98/2 | 99 |
| Example 22 | 1 | 9 | 55 | 4 | 200 | 30 | 44 | 98/2 | 98 |
| Comp. Ex. 1 | 1 | 9 | 55 | 4 | 180 | 66 | 55 | 98/2 | 99 |
| Comp. Ex. 2 | 1 | 9 | 55 | 4 | 170 | 26 | 42 | 92/8 | 98 |

*1: Propylene origomer having a terminal vinyl group
*2: Propylene origomer having a terminal vinylidene group
*3: 4-methyl-1-penten
*4: Total Pressure As apparent from the results of the Examples and Comparative Examples, according to the present invention, a propylene oligomer can be produced without using expensive aluminoxane or with use of a small amount of an organoaluminum compound since the catalyst activity per aluminum unit is high, resulting in cost reduction. Further, the process according to the present invention is advantageous in omitting or simplifying the deashing step during the production of oligomers.

What is claimed is:

1. A process for producing propylene based oligomer which comprises polymerizing propylene alone or propylene and an olefin other than propylene in the presence of a catalyst comprising:

(A) a transition metal compound represented by the general Formula (I):

$$(R_5C_5)_m MX_{4-m} \quad (I)$$

wherein $R_5C_5$ is a hydrocarbon group-substituted cyclopentadienyl group which is the same as or different from any other $R_5C_5$; M is a zirconium atom or hafnium atom; X is the same as or different from each other and is a hydrogen atom, halogen atom or hydrocarbon group; m is an integer of from 1 to 4; and (B) a compound capable of forming an ionic complex when reacted with the transition metal compound selected from the group consisting of compounds having the formula (II), (III), and (IV):

$$([L^1-H]^{g+})_h([M^2X^1X^2\ldots X\eta]^{(n-o)-})_i \quad (II)$$

$$([L^2]^{g+})_h([M^3X^1X^2\ldots X\eta]^{(n-o)-})_i \quad (III)$$

$$([L^1-Z]^{g+})_h([M^2X^1X^2\ldots X\eta]^{(n-o)-})_i \quad (IV)$$

wherein $L^1$ is a Lewis base; $L^2$ is $M^4$, $R^2R^3M^5$ or $R^4{}_3C$; Z is a hydrocarbon group selected from the group consisting of an alkyl group, aryl group, arylalkyl group and alkylaryl group; $M^2$ and $M^3$ are independently elements selected from the groups of VB, VIB, VIIB, VIII, IB, IIB, IIIA, IVA and VA of the Periodic Table; $M^4$ is a transition metal, $M^5$ is a metal selected from the VIII group of the Periodic Table; $X^1$ to $X^n$ are independently a hydrogen atom, dialkylamino group, alkoxy group, aryl group, substituted aryl group, aryloxy group, alkyl group, substituted alkyl group, organometalloid group or halogen atom; $R^2$ and $R^3$ are independently cyclopentadienyl group, substituted cyclopentadienyl group, indenyl group or fluorenyl group; $R^4$ is an alkyl group, substituted alkyl group, aryl group, substituted aryl group, arylalkyl group, substituted arylalkyl group, alkylaryl group or substituted alkylaryl group; R4 is the same as or different from each other; o is a valency of $M^2$ and $M^3$ is an integer of 1 to 7; n is an integer of 2 to 8; g is an ion value number and is an integer of 1 to 7; h is an integer of at least 1; and i is specified by the formula: $i = h \cdot g/(n-o)$.

2. The process according to claim 1, wherein the catalyst further comprises (C) an organoaluminum compound in addition to Compound (A) and Compound (B).

3. The process according to claim 1, wherein the polymerization is conducted in the presence of hydrogen.

4. The process according to claim 1, wherein $M^4$ is a transition metal selected from groups IB, IIB, or VIII of the Periodic Table.

* * * * *

UNITED STATES PATENT AND TRADEMARK OFFICE
CERTIFICATE OF CORRECTION

PATENT NO. : 5,171,919
DATED : December 15, 1992
INVENTOR(S) : Masami WATANABE et al It is certified that error appears in the above-identified patent and that said Letters Patent is hereby corrected as shown below:

In Table 2 in column 9-10, under the column entitled "Kind of Comonomer", on the line 37, Example 14, change " 1-ブテン " to to --1-butene;

on the line 39, Example 15, change " 1-ブテン " to --1-butene--;

on the line 41, Example 16, change " 1-ペンテン " to --1-pentene--;

on the line 43, Example 17, change " 1-ヘキセン " to --1-hexene--; and on the line 45, Example 18, change " 1-ブテン " to --1-butene--.

Signed and Sealed this

Twenty-second Day of February, 1994

Attest:

BRUCE LEHMAN

Attesting Officer        Commissioner of Patents and Trademarks